United States Patent [19]

Ooi et al.

[11] Patent Number: 4,567,147

[45] Date of Patent: Jan. 28, 1986

[54] ATTENUATED SMALLPOX VACCINE STRAIN

[75] Inventors: Kiyoshi Ooi, Tokyo; Michio Morita, Chiba; Kazuyoshi Suzuki, Ichikawa; Soh Hashizume, Chiba; Hanako Yoshizawa, Funabashi, all of Japan

[73] Assignee: Chiba Prefectural Government, Chiba, Japan

[21] Appl. No.: 683,867

[22] Filed: Dec. 20, 1984

[30] Foreign Application Priority Data

Mar. 28, 1984 [JP] Japan .................................. 59-58502

[51] Int. Cl.$^4$ ...................... C12N 7/08; A61K 39/285
[52] U.S. Cl. ....................................... 435/237; 424/89
[58] Field of Search ........................... 424/59; 435/237

[56] References Cited

U.S. PATENT DOCUMENTS 3,135,661  6/1964  Bartell et al. ..................... 424/89
3,739,065  6/1973  Thorishaus ....................... 424/89

Primary Examiner—Sam Rosen
Attorney, Agent, or Firm—Holman & Stern

[57] ABSTRACT

The present invention discloses an attenuated smallpox vaccine strain exhibiting antibody production similar to conventional strains but without postvaccinal side effects. The vaccine is prepared by attenuating a Lister strain of a vaccinia virus by cell culture and selecting a suitable strain therefrom showing relatively small and uniform pocks on the chorioallantoic membrane of an embryonated egg.

1 Claim, 2 Drawing Figures

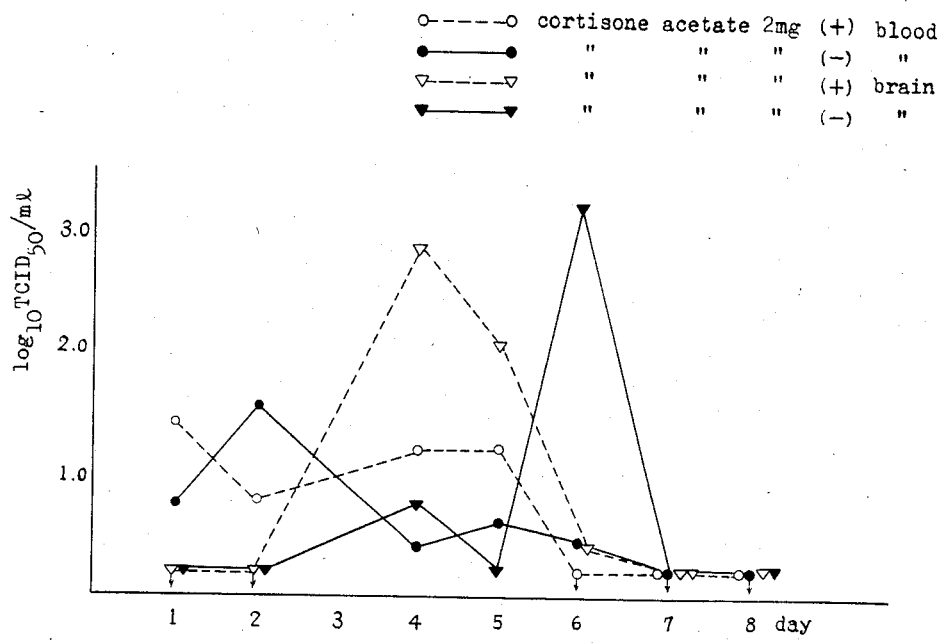
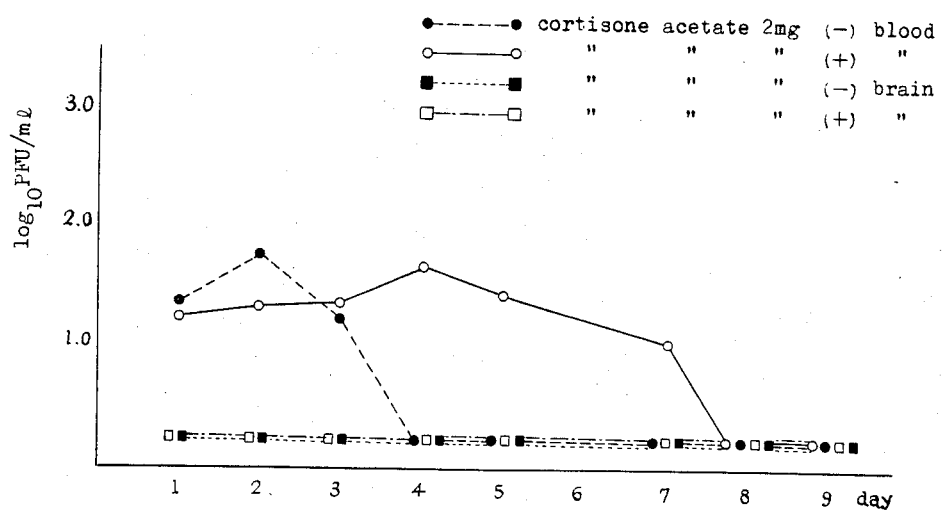

ATTENUATED SMALLPOX VACCINE STRAIN

DETAILED DESCRIPTION OF THE INVENTION

This invention relates to a vaccine strain exhibiting a similar antibody productivity to that of conventional strains and little postvaccinal side effects, which is prepared by attenuating a Lister strain of a vaccinia virus by cell culture.

(1) Preparation of the Strain of the Present Invention

The original strain (i.e. Lister strain) was subcultured in rabbit Kidney cells over 36 generations at 30° C. and then plaque-purified thrice to isolate 50 clones. From these 50 clones, a temperature-sensitive variant which showed the worst growth at 40° C. in Vero cells established from green monkey (Coropithecus aethiops) Kidney cells was selected. Compared with the original strain, the temperature-sensitive variant grew better in rabbit Kidney cells but worse in rabbit central nervous system cells. In the central nervous system of a monkey, it exhibited a pathogenicity which was similar to that of $DI_s$ strain, i.e. an attenuated micropock variant prepared from Dairen 1 strain, and extremely lower than that of the original strain. Accordingly an inoculation test was carried out with the use of a small number of subjects. Consequently it was found that the foregoing variant would result in a light systemic reaction with a febrility ratio of 14% followed by somewhat slow formation of crust. Therefore it was attempted to isolate a clone showing a poor skin growth capacity. As a marker in the isolation of the foregoing clone, the size of pocks on the chorioallantoic membrane of an embryonated egg was employed. That is, the temperature-sensitive variant was subcultured in rabbit Kidney cells over six generations and plaque-purified twice to isolate a clone showing relatively small and uniform pocks on the chorioallantoic membrane of an embryonated egg. The clone was further subcultured in rabbit Kidney cells over additional three generations at 30° C. to isolate a clone showing extremely small pocks on the chorioallantoic membrane of an embryonated egg to thereby prepare an attenuated smallpox vaccine strain.

(2) Properties of the Strain of the Present Invention

Properties of the strain of the present invention are summarized in Table 1 compared with those of the original strain (i.e. Lister strain).

As shown in Table 1, the strain of the present invention has many markers available in tests in vitro and exhibit a lower pathogenicity in the central nervous systems of rabbits and cynomolgus monkeys (Macaca fascicularis), no invasiveness caused by peripheral infection on the central nervous system of mice and a poor skin growth capacity in rabbits and human. These properties suggest that it is available as a smallpox vaccine strain.

TABLE 1

Properties of Lister strain and the strain of the present invention

| | Lister strain | Strain of the invention |
|---|---|---|
| Ingrowable temperature in rabbit Kidney cells | 41° C. or above | 40.5° C. |
| Plaque size in rabbit Kidney cells | large | medium |
| Pock size | large | medium |
| Growability in chorio-allantoic membrane of an embryonated egg | +++ | +++ *1 |
| Growability in Vero cells | +++ | + *1 |
| Pathogenicity in central nervous system | | |
| Rabbit *2 | +++ | + |
| Cynomolgus monkey *3 | yes (died) | no (survival) |
| Invasiveness by peripheral infection of central nervous system *4 | | |
| Mouse (cortisone acetate, subcutaneous inoculation) | yes | no |
| Mouse (untreated) | yes | no |
| Skin growth capacity | | |
| Rabbit | +++ | + |
| Human | ++ | + |

*1 They differ from each other by $2\log_{10}$.
*2 Evaluated from the amount of recovered virus six days after intracerebral inoculation of $10^{6.7}$ $TCID_{50}$ of a virus.
*3 Evaluated by intrathalmic inoculation of $10^{8.5}$ $TCID_{50}$ of a virus.
*4 Mice treated or untreated with cortisone acetate were intraabdominally inoculated with $10^{7.3}$ PFU of a virus and the amounts of intracerebral virus thereof were determined.
Results are shown in FIGS. 1 and 2.

The antibody productivity of the strain of the present invention in a rabbit was compared with that of the Lister strain. Table 2 shows the results. In spite of the poor skin growth capacity, the strain of the present invention brought about similar increase and continuance in both hemagglutination inhibitting antibody titer and neutralizing antibody titer to those of the Lister strain.

TABLE 2

| | Change in antibody titers | | | |
|---|---|---|---|---|
| | Hemagglutination inhibitting antibody titer | | Neutralizing antibody titer | |
| Weeks after inoculation | Lister strain | Strain of invention | Lister strain | Strain of invention |
| 2 | $2^{6.5}$ | $2^{4.5}$ | $4^{4.9}$ | $4^{4.9}$ |
| 4 | $2^{6.5}$ | $2^{5.0}$ | $4^{4.9}$ | $4^{4.7}$ |
| 6 | $2^{4.5}$ | $2^{5.0}$ | $4^{5.0}$ | $4^{4.6}$ |
| 13 | $2^{3.5}$ | $2^{5.5}$ | $4^{5.0}$ | $4^{4.7}$ |

Note: Each strain was inoculated in an amount of $10^{8.0}$ PFU.

(3) Determination of Infectivity Titer

Vero cells which have been generally used in determining infectivity titers of vaccinia viruses are unsuitable in determining the infectivity titer of the strain of the present invention because of the poor sensitivity thereto. On the other hand, the pock method with the use of the chorioallantoic membrane of an embryonated egg is highly sensitive to the strain of the present invention although it has been pointed out that various factors such as the viral dilution, variation between embryonated eggs and variation in the techniques of workers would result in a poor reproducibility of this method. The plaque method with the use of chick embryo cells which is employed herein is somewhat less sensitive than the pock method, but results in infectivity titers of a high reproducibility. Therefore the latter is an effective method in determining the infectivity titer of the strain of the present invention. The result of an examination on the correlativity and reliability of the pock and plaque methods is as follows.

TABLE 3

Comparison of infectivity titers determined by pock and plaque methods

| Smallpox vaccine strain | Pock PFU/ml | Plaque PFU/ml |
|---|---|---|
| Lister strain | $1.19 \times 10^8$ | $1.38 \times 10^7$ |
| " | $4.97 \times 10^7$ | $1.43 \times 10^7$ |
| Strain of the invention | $2.77 \times 10^8$ | $5.56 \times 10^7$ |
| " | $1.47 \times 10^8$ | $2.90 \times 10^7$ |
| " | $1.33 \times 10^8$ | $5.69 \times 10^7$ |
| " | $1.13 \times 10^8$ | $3.0 \times 10^7$ |
| " | $1.51 \times 10^6$ | $5.49 \times 10^5$ |
| $DI_s$ strain | $1.44 \times 10^6$ | $2.00 \times 10^5$ |
| " | $9.77 \times 10^5$ | $2.27 \times 10^5$ |

Table 3 shows the infectivity titers of the Lister strain of vaccinia virus, the strain of the present invention and a $DI_s$ strain of the same virus simultaneously determined by these two methods. The correlation coefficient $\gamma$ calculated by logarithmic infectivity titers determined by these two methods is 0.984. As a result of a test of significance of the correlation, $t_0$ is determined to be 14.52 which is larger than $t_{f=7} = (\alpha = 0.001) = 54.08$, suggesting that the infectivity titers determined by these two methods closely relate to each other. The regression equation of these infectivity titers determined by these two methods is $y_1 = 0.838 + 0.971 y_2$, wherein $y_1$ ($\log_{10} TCID_{50}/ml$) represents infectivity titers determined by the pock method while $y_2$ ($\log_{10} TCID_{50}/ml$) represents those determined by the plaque method.

In order to examine the reliability of these two methods, variance of the data obtained by these methods were compared with each other. Table 4 (A) shows the data obtained by measuring solutions prepared by appropriately diluting the same strains as used in Table 3 by these two methods. Variance and variant ratio of these data of each virus were determined for F calibraliton to thereby test the significance of the variance between these two methods. Results is shown in Table 4 (B).

TABLE 4

Data obtained by pock and plaque methods and variant ratio thereof

| | A | | B | | | |
|---|---|---|---|---|---|---|
| | pock method | plaque method | variance | | | |
| Smallpox vaccine strain | number of pocks /0.1 ml | number of plaques /0.1 ml | pock method ($S_1^2$) | plaque method ($S_2^2$) | variant ratio $F_0 = S_1^2/S_2^2$ | F $\alpha = 0.05$ |
| Lister strain | 31.34.35.38.39 50.57.68.70.75 | 24.24.27.28 31.31.32.32 | 278.2 | 11.41 | 24.38 | $f_1 = 9\ f_2 = 7$ 3.677 |
| Strain of the invention | 40.41.42.59 61.62.63.75 | 13.17.18.21.22 22.23.23.25.39 | 164.8 | 46.9 | 3.515 | $f_1 = 7\ f_2 = 9$ 3.293 |
| Strain of the invention | 14.34.35.52.52 52.62.73.78 | 29.29.31.32.37 37.38.40.43.50 | 405.7 | 44.6 | 9.096 | $f_1 = 8\ f_2 = 9$ 3.230 |
| $DI_s$ strain | 26.29.37.44 62.71.73 | 19.20.20.22 24.25.29 | 387.8 | 12.57 | 30.85 | $f_1 = 6\ f_2 = 6$ 4.284 |
| $DI_s$ strain | 13.14.20.23.25 27.36.38.42.49 | 7. 7. 8. 8 8. 8. 10 | 146.2 | 1.0 | 146.2 | $f_1 = 9\ f_2 = 6$ 4.099 |

Consequently $F_0$ is larger than F ($\alpha = 0.05$) in all viral samples. That is to say, there is a significant difference in the variance at a ratio of risk of 5%, which suggests that the pock method would bring about higher variant than the plaque method in determining the infectivity titer of a vaccinia virus. Accordingly these two methods closely correlate to each other and the latter is much more reliable than the former.

However, these two methods may be selected case by case. For example, it is preferable to employ the plaque method in comparing infectivity titers, while it is preferable to employ the pock methods in determining absolute infectivity titers.

EXAMPLE

Preparation of Dried Smallpox Vaccine in Cell Culture

A conventional process for preparing a variola vaccine comprises inoculating bovine skin with a vaccinia virus and scratching a portion on which pocks are formed to thereby use it as a vaccine in the form of an emulsion. However, the vaccine thus prepared may be contaminated with various bacteria, mycoplasma and viruses other than the vaccinia virus. It is very difficult to prepare the vaccine not contaminated with any microorganism. On the contrary, the cell cultured vaccine prepared from the strain of the present invention may be contaminated with no microorganism. Adding to the ideal property from a viewpoint of quality control, the vaccine thus prepared is superior to conventional ones in postvaccinal side effects and complicating diseases. Furthermore the cell cultured vaccine prepared from the strain of the present invention is superior to conventional methods for vaccination with the use of the chorioallantoic membrane of an embryonated egg or bovine skin from an economical viewpoint and may be lyophilized by diluting with a medium and adding an appropriate stabilizer.

(4) Process for the Preparation (1) Cell culture

A kidney of a rabbit aged three weeks or younger was removed, cut into pieces under a sterile condition, digested with a 0.25% solution of trypsin and suspended in a medium for cell-growth containing 10% of Calf serum to give a concentration of $3 \times 10$ cells/ml. 200 ml portions of the medium were introduced into bottles and subjected to roller bottle culture at 37° C. for four days.

(2) Culture of virus

After removing the medium, the surface of the cells was washed with a saline solution twice and each roller culture bottle was inoculated with 10 ml ($1.55 \times 10^7$ PFU/ml) of the strain of the present invention followed by adsorption at 30° C. for two hours. Then 100 ml of a 199 medium containing 0.2% of gelatin was added and the mixture was cultured at 30° C. for two or three days. After shaking the cells off from the bottle, the cell suspension was centrifuged at 2,000 rpm for 10 min. After removing the supernatant, the cells were resuspended in 10 ml of a 199 medium containing 0.2% of gelatin.

(3) Extraction of virus

The cell suspension was ultrasonically treated and centrifuged at 2,000 rpm for 10 min. The supernatant thus separated was employed as the bulk material of the vaccine.

(4) Determination of infectivity titer

The chorioallantoic membrane of an embryonated egg aged 11 days was inoculated with the viral solutions and cultured at 37° C. for two days. Pocks thus formed were counted to culculate the infectivity titer per ml. The infectivity titer of the pool cell extract was $1.7 \times 10^8$ PFU/ml.

(5) Lyophilization

The virus extracted from the cells was diluted with a 199 medium and sorbitol and peptone were added thereto to give a final concentration of 5% each. 0.7 ml portions of the obtained solution were introduced into vial bottles and lyophilized with a vacuum lyophilizer. Table 5 shows the result.

TABLE 5

| Result of lyophilization | | | |
|---|---|---|---|
| Infectivity titer (PFU*/ml) | | | |
| before lyophilization | after lyophilization | lowering | Moisture content |
| $1.7 \times 10^8$ | $1.5 \times 10^8$ | 1/1.2 | 0.9–1.8 |

*pock forming units (6) Shelf stability of lyophilized vaccine

The lyophilized vaccine was subjected to an accelerated denaturation test by storing at 30° C., 37° C., 50° C. and 60° C. thus estimating the decrease in the infectivity titer and comparing it with the minimum requirement of biological products as well as that of a test of the stability of cell cultured smallpox vaccine. Each sample was collected three or four times depending on the temperature at which it was stored. Infectivity titers of samples in two vial bottles were evaluated each time separately. Table 6 shows the result.

TABLE 6

Infectivity titer of samples stored at various temperature vs. time

| Heating period | Infectivity titer and decrease | | | | |
|---|---|---|---|---|---|
| 30° C. | 0 | 2 weeks | 4 weeks | 23.6 weeks | |
| | $5.40 \times 10^7$* | $2.73 \times 10^7$ 1/2.0** | $2.39 \times 10^7$ 1/2.3 | $4.83 \times 10^6$ 1/11.2 | |
| | | $3.09 \times 10^7$ 1/1.7 | $2.42 \times 10^7$ 1/2.2 | $5.86 \times 10^6$ 1/9.2 | |
| 37° C. | 0 | 1 week | 4 weeks | 7 weeks | 23.6 weeks |
| | $5.40 \times 10^7$ | $3.11 \times 10^7$ 1/2.1 | $1.40 \times 10^7$ 1/3.9 | $1.00 \times 10^7$ 1/5.1 | $1.67 \times 10^6$ 1/32.4 |
| | | $5.71 \times 10^7$ 1/0.9 | $1.11 \times 10^7$ 1/4.9 | $8.15 \times 10^6$ 1/6.6 | $1.68 \times 10^6$ 1/32.0 |
| 50° C. | 0 | 4 days | 9 days | 17 days | 4 weeks |
| | $5.40 \times 10^7$ | $1.09 \times 10^7$ 1/5.0 | $5.75 \times 10^6$ 1/9.4 | $1.72 \times 10^6$ 1/31.4 | $1.11 \times 10^6$ 1/48.8 |
| | | $7.79 \times 10^6$ 1/6.9 | $4.05 \times 10^6$ 1/13.3 | $4.75 \times 10^6$ 1/11.4 | |
| 60° C. | 0 | 2 days | 4 days | 9 days | 17 weeks |
| | $5.40 \times 10^7$ | $2.31 \times 10^6$ 1/23.4 | $3.30 \times 10^6$ 1/16.4 | $3.26 \times 10^5$ 1/16.6 | $1.13 \times 10^5$ 1/477 |
| | | $3.05 \times 10^6$ 1/17.7 | $9.93 \times 10^5$ 1/54.3 | $2.05 \times 10^5$ 1/26.4 | $7.98 \times 10^3$ 1/6723 |

*plaque forming units (PFU)/ml
**decrease in the infectivity titer based on that at the initiation.

The residual infectivity titer of the sample stored at 37° C. for four weeks was 1/44 and higher than the minimum requirement of biological products (1/10). The infectivity titer thereof was $10^{7.8}$ PFU/ml and also higher than the minimum requirement of biological products ($10^{7.7}$ PFU/ml). Therefore both of these two values satisfy the minimum requirement of biological products.

Decreases in the infectivity titers at these temperatures were calculated according to the equation of an accelerated denaturation test based on the data as shown in Table 6. Table 7 shows the result.

TABLE 7

| Presumed temp. for storage | Estimated shelf stability by accelerated denaturation test: 20%-decrease period | Half-value period |
|---|---|---|
| −70° C. | $6.2 \times 10^5 \sim 7.6 \times 10^8$ years* | $1.9 \times 10^6 \sim 2.4 \times 10^9$ years* |
| −15° | 14.8 ~ 266 years | 45.9 ~ 828 years |
| 5° | 320 days ~ 5.1 years | 2.7 ~ 160 years |
| 15° | 90.1 ~ 321 days | 280 days ~ 2.7 years |
| 25° | 27.7 ~ 61.7 days | 86 ~ 190 days |
| 37° | 7.4 ~ 9.8 days | 23.1 ~ 30.5 days |

*a confidence interval of 95%.

The 20%-decrease period and half-value period of the sample stored at −15° C. were longer than 14 years and 45 years respectively, which suggests that the vaccine may be stored for a long time.

(5) Field Test of the Strain of the Present Invention

In order to examine the presence of postvaccinal side effects and complicating diseases caused by the strain of the present invention based on the antibody productivity thereof, a field test was carried out with the guidance of the Ministry of Health and Welfare of Japan. The result will now be summarized.

(1) Antibody production

The antibody productivity of the strain of the present invention was compared with those to the Lister strain and the CV-1 strain which has been subcultured in chick embryo cells at New York City Department of Health Laboratory. Table 8 shows the result.

TABLE 8

Antibody production after inoculation of various smallpox vaccine strains

| Smallpox vaccine strain | Time (month) | Number of subjects | HI antibody titer |
|---|---|---|---|

TABLE 8-continued

| Smallpox vaccine strain | Time (month) | Number of subjects | Antibody production after inoculation of various smallpox vaccine strains | | | | | | | | |
|---|---|---|---|---|---|---|---|---|---|---|---|
| | | | $<2 \sim 4$ | 2 | 4 | 8 | 16 | 32 | 64 | 128 | average |
| Strain of invention | $1 \sim 1\frac{1}{2}$ | 513 | 18 | 12 | 88 | 161 | 155 | 72 | 6 | 1 | $2^{3.3}$ |
| | $3 \sim 6$ | 19 | 1 | 3 | 3 | 2 | 2 | 6 | | | $2^{3.2}$ |
| CV-1 | $1 \sim 1\frac{1}{2}$ | 26 | | | 1 | 7 | 11 | 7 | | | $2^{3.9}$ |
| | $3 \sim 6$ | 25 | | | 2 | 10 | 11 | 1 | 1 | | $2^{3.6}$ |
| Lister | $1 \sim 1\frac{1}{2}$ | 7 | | | | | 5 | 2 | | | $2^{4.3}$ |
| | $3 \sim 6$ | 19 | | | 4 | 5 | 8 | 2 | | | $2^{3.4}$ |
| | | | NT antibody titer | | | | | | | | |
| | | | $<4^{0.9}$ | $4^{1.0}\sim$ | $4^{1.5}\sim$ | $4^{2.0}\sim$ | $4^{2.5}\sim$ | $4^{3.0}\sim$ | $4^{3.5}\sim$ | $4^{4.0}\sim$ | average |
| Strain of invention | $1 \sim 1\frac{1}{2}$ | 97 | | 5 | 10 | 25 | 37 | 18 | 2 | | $4^{2.5}$ |
| CV-1 | $1 \sim 1\frac{1}{2}$ | 6 | 1 | | 2 | 2 | | 1 | | | $4^{1.9}$ |
| | $3 \sim 6$ | 11 | 1 | 1 | 4 | 2 | 3 | | | | $4^{2.0}$ |
| Lister | $1 \sim 1\frac{1}{2}$ | 5 | | | | 3 | 2 | | | | $4^{2.4}$ |
| | $3 \sim 6$ | 12 | 1 | 2 | | 2 | 7 | | | | $4^{2.2}$ |

As shown in Table 8, both of the hemagglutination inhibitting (HI) and neutralizing (NT) antibody titers suggest that the strain of the present invention would have a similar or superior antibody productivity to those of the Lister and CV-1 strains. As a result of a booster with the Lister strain to 561 subjects previously inoculated with the strain of the present invention and an immunological examination on their topical reacitons, it was found that sufficient immunity would be obtained by the inoculation with the strain of the present invention.

(2) Abnormality in brain waves

A brain wave test was performed on those showing positive reactions two weeks after the inoculation with the strain of the present invention or the Lister strain. Consequently five subjects among 19 (26.3%) inoculated with the Lister strain exhibited temporary abnormality in brain waves while those inoculated with the strain of the present invention exhibited no abnormality, which suggests that the latter strain has a low neurotropsy.

(3) Postvaccinal side effects and complicating diseases

Approximately fifty thousands children have been inoculated with the strain of the present invention without any serious side effects nor complicating diseases. 10,578 children among them were clinically followed in detail after the inoculation. Tables 9 and 10 show the ratios of positive reaction by age, febrility and complicating diseases.

TABLE 9

Ratio of positive reaction and febrility caused by the strain of the present invention by age

| | | | Those showing positive reaction and examined systemic reaction for 14 days or longer | | | | | | |
|---|---|---|---|---|---|---|---|---|---|
| Age | Number of subjects | Number of the subjects showing positive reaction | Number of subjects | Number of subjects attacked with fever after 4 to 14 days | Basal temperature | | | | un-known |
| | | | | | $37.5\sim$ | $38.0\sim$ | $39.0\sim$ | $40.0\sim$ | |
| 0 | 11 | 11 | 11 | 0 | 0 | 0 | 0 | 0 | 0 |
| 1 | 687 | 669 | 632 | 69 | 14 | 42 | 11 | 0 | 2 |
| $2 \sim 4$ | 6,800 | 6,496 | 6,094 | 474 | 139 | 219 | 88 | 6 | 22 |
| $>5$ | 2,040 | 1,900 | 1,807 | 120 | 42 | 57 | 17 | 3 | 1 |
| Total | 9,538 | 9,075 (95.2%) | 8,544 | 663 (7.8%) | 195 (29.4) | 318 (48.0) | 116 (17.5) | 9 (1.4) | 25 (3.8) |

| | Those showing positive reaction and examined systemic reaction for 14 days or longer | | | | | Other reactions | | | |
|---|---|---|---|---|---|---|---|---|---|
| | Febrility period | | | | | | Auto-inocu-lation | Secondary vacciniae vesicle | |
| Age | 1 day | 2 days | 3 days | 4 days | un-known | Eczema vaccinatum | | | exanthema | Heat cramps |
| 0 | | | | | | | | | | |
| 1 | 33 | 19 | 8 | 8 | 1 | 1 | 2 | 1 | 3 | 1 |
| $2 \sim 4$ | 288 | 115 | 38 | 25 | 8 | | 6 | 25 | 5 | 2 |
| $>5$ | 81 | 28 | 5 | 6 | | | 1 | 2 | | |
| Total | 402 (60.6) | 162 (24.4) | 51 (7.7) | 39 (5.9) | 9 (1.4) | 1 | 9 | 28 | 8 | 3 |

TABLE 10

Comparison of reactions caused by various smallpox vaccine strains

| Variola vaccine strain | Number of subjects | Ratio of positive reaction | Average rubor size (mm) | Average induration size (mm) | Febrility ratio (%) |
|---|---|---|---|---|---|
| Lister strain | 3,662 | 93.7 | 17.6 | 15.3 | 26.6 |
| CV-1 | 22,976 | 92.4 | 21.1 | 16.8 | 8.5 |
| Strain of the | 10,578 | 95.1 | 18.4 | 6.1 | 7.7 |

TABLE 10-continued

Comparison of reactions caused by various smallpox vaccine strains

| Variola vaccine strain | Number of subjects | Ratio of positive reaction | Average rubor size (mm) | Average induration size (mm) | Febrility ratio (%) |
|---|---|---|---|---|---|
| invention | | | | | |

The ratio of positive reaction, the febrility ratio and the incidence of complicating skin diseases caused by the strain of the present invention were 95.2%, 7.8% and 0.19%, respectively. No complicating disease was observed in the central nervous system. The ratio of positive reaction caused by the strain of the present invention is similar to those caused by conventional smallpox vaccine strains, while the febrility ratio of the former is significantly lower than the latter. It might be further assumed that the incidences of postvaccinal encephalopathy and encephalitis caused by the former would be lower than those caused by the latter although the number of examples was not so large. Furthermore the strain of the present invention was superior in the average induration size as shown in Table 10.

Apart from the abovementioned purpose for preventing smallpox by the inoculation of a vaccinia virus, the strain of the present invention is further available in a recombinant DNA experiment wherein a recombination vaccinia virus containing foreign proteins is constructed by inserting DNA of an expressed polypeptide into the DNA of the vaccinia virus.

Since the strain of the present invention would exhibit no invasiveness caused by peripheral infection on the central nervous system of a mouse, little postvaccinal side effects and no postvaccinal encephalopathy nor encephalitis, it may be very advantageously employed in constructing the abovementioned recombination vaccinia virus.

BRIEF DESCRIPTION OF THE DRAWINGS

FIG. 1 is a diagram of the recovery of the virus from the blood and brain of a mouse inoculated with the Lister strain. FIG. 2 is a diagram of the recovery of the virus from the blood and brain of a mouse inoculated with the strain of the present invention.

We claim:

1. An attenuated smallpox vaccine strain exhibiting no invasiveness caused by peripheral infection on the central nervous system of a mouse and little post-vaccinal side effects, which is prepared by subculturing a Lister strain of vaccinia virus in rabbit kidney cells over 36 generations at 30° C., plaque-purifying the strain thrice to isolate 50 clones, selecting a temperature-sensitive variant showing worst growth in Vero cells at 40° C. from said 50 clones, subculturing the temperature sensitive variant in rabbit kidney cells over six generations, plaque-purifying the variant twice to isolate a clone showing relatively small and uniform pocks on the chorioallantoic membrane of an embryonated egg, subculturing the clone in rabbit kidney cells over three generations at 30° C. and isolating a clone showing very small pocks on the chorioallantoic membrane of an embryonated egg.

* * * * *